US00PP17972P2

(12) United States Plant Patent
Corley

(10) Patent No.: US PP17,972 P2
(45) Date of Patent: Sep. 4, 2007

(54) ***RAPHIOLEPIS* HYBRID PLANT NAMED 'WILCOR'**

(50) Latin Name: ***Raphiolepis* hybrid *delacourii***
Varietal Denomination: Wilcor

(75) Inventor: Will Lee Corley, Griffin, GA (US)

(73) Assignee: Plant Development Services Inc., Loxley, AL (US)

( * ) Notice: Subject to any disclaimer, the term of this patent is extended or adjusted under 35 U.S.C. 154(b) by 424 days.

(21) Appl. No.: 11/097,900

(22) Filed: Apr. 4, 2005

(51) Int. Cl.
*A01H 5/00* (2006.01)

(52) U.S. Cl. ..... Plt./254
(58) Field of Classification Search ..... Plt./254
See application file for complete search history.

*Primary Examiner*—Kent Bell
*Assistant Examiner*—Annette H Para

(57) ABSTRACT

A new and distinct variety of *Raphiolepis×delacourii* found as an openly pollinated seedling of *Raphiolepis×delacourii* 'Georgia Charm' U.S. Plant Pat. No. 9,982. The new variety is unique with its dense, mounding growth habit, resistance to Entomosporium leaf spot, increased cold hardiness, and abundance of late blooming white flowers.

1 Drawing Sheet

Genus species: *Raphiolepis* hybrid *delacourii*.
Varietal denomination: 'Wilcor'.

BACKGROUND OF THE INVENTION

The present invention relates to a new and distinct variety of the genus *Raphiolepis* and a member of the Rosaceae family. This new *Raphiolepis* variety, hereinafter referred to as 'Wilcor' was discovered by Will Lee Corley in May, 1995. 'Wilcor' was found as an openly pollinated seedling of *Raphiolepis×delacourii* 'Georgia Charm' U.S. Plant Pat. No. 9,982. Mr. Corley found the seedling at the University of Georgia Experiment Station at Griffin, Ga. The value of this new cultivar lies in its dense, mounding growth habit, resistance to Entomosporium leaf spot, increased cold hardiness, and abundance of late-blooming white flowers. The new variety has retained many of the outstanding attributes of its parent cultivar, in particular its tolerance of heat, drought, salt, and disease, which makes it adaptable to culture in most of the Sunbelt States. As with the parent cultivar, the plant of this invention may be advantageously employed as a specimen appointment, a ground cover, in either formal or informal groupings, and is quite attractive in mass plantings. 'Wilcor' serves well in foundation plantings and is adaptable for culture as a potted plant. 'Wilcor' is responsive to pruning and training and may be employed in forming dense, attractive hedges, and maintained without an excessive amount of care. This plant is easy to care for and maintain in size due to its short internodes, heavy branching, and dense canopy. Its natural propensity to remain small to maturity makes it valuable for landscape uses in smaller home gardens which requires plants that do not outgrow their intended mature dimensions.

Asexual propagation of the new plants by cuttings has been under Mr. Corley's direction in Griffin, Ga. The new plant retains its distinctive characteristics and reproduces true to the type in successive generations. The plant cannot be reproduced true from seed.

SUMMARY OF THE INVENTION

The following are the most outstanding and distinguishing characteristics of this new cultivar when grown under normal horticultural practices in Griffin, Ga.

1. Dense and mounding in nature. Plant is wider than tall.
2. Mature leaves are a lustrous dark green color.
3. Moderate to slow growth rate, requiring little pruning.
4. Hardy to Zone 7b.
5. Heat and drought tolerant.
6. Adaptable to a wide range of soil types.
7. Good plant for coastal areas because of wind and salt tolerance.
8. Has shown good resistance to leaf spot.
9. Relatively pest resistant.
10. Good specimen plant.
11. Good foundation plant.
12. Makes a very good low-growing hedge.
13. Very desirable in planters.
14. The flowers are single, white, fragrant, profuse, and late-blooming.
15. Produces seeds and therefore may result in bird visitations.

DESCRIPTION OF THE DRAWINGS

This new *Raphiolepis* hybrid variety is illustrated by the accompanying photographic prints in which:

1. The photograph at the top of the sheet is a close-up showing the flower, buds, foliage and stem color, as well as flower size and form.

2. The photograph at the bottom of the sheet shows the dense and mounding growth habit of a three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Raphiolepis* based on my observations made of two year old plants grown in three gallon containers in commercial production practices, in greenhouses, and in established landscape plantings in Griffin, Ga.

Distinctive Characteristics:

TABLE 1

| Characteristic | *Raphiolepis* X 'Wilcor' | *Raphiolepis* X 'Georgia Charm' | *Raphiolepis* X 'Eskimo' | *Raphiolepis* X 'Ovata' |
|---|---|---|---|---|
| Height (Mature) | 2–3' | 3–4' | 5–6' | 4–6' |
| Width (Mature) | 3–4' | 4–5' | 7–8' | 4–6' |
| Leaf Length | 2 1/8–2 5/8" | 1 3/4–2" | 1 7/8–2 1/8" | 1–1 1/2" |
| Leaf Width | 1–1 3/8" | 5/8–7/8" | 5/8–7/8" | 3/4–1 1/4" |
| Leaf Margin | Entire to distally serrate | Distally serrate | Serrate to crenate | Serrate to crenate |
| Leaf Curvature | Almost flat | Almost flat | Slightly wavy | Almost flat |
| Leaf Shape | Elliptic-obovate | Elliptic-obovate | Elliptic-obovate | Ovate-broad ovate |
| Flower Color | White | White | Light pink | White |
| Bloom Period | Late April-Mid May | Mid-Late April | Mid-Late April | Mid-Late April |
| Hardy Zone | 7b | 7b | 7b | 7b |
| Leaf Spot Resistance | High | High | High | High |

Each of the cultivars, 'Wilcor', 'Georgia Charm', and 'Eskimo' are cultivars of Rosaceae *Raphiolepis* hybrid *delacourii,* The author of the genus name *Raphiolepis* is John Lindley (1799–1865). The species *delacourii* was named by Edouard Francois Andre (1840–1911). This hybrid was first reported in the late nineteenth century by a gardener named Delacour in Cannes, France and is an apparent hybrid of *Raphiolepis umbellata* and *Raphiolepis indica. Raphiolepis umbellata* 'Ovata' is also in the Rosaceae family. The author of the species name *umbellata* is Carl Pehr Thunberg (1743–1824) and the author of the cultivar 'Ovata' is Charles Briot (1804–1888).

Extensive breeding work has been performed at the University of Georgia Experiment Station at Griffin, Ga. to produce *Raphiolepis* cultivars with increased resistance to Entomosporium maculatum leaf spot and increase cold hardiness. The varieties *Raphiolepis×delacourii* 'Eskimo' (unpatented) and *Raphiolepis umbellata* 'Ovata' (unpatented) were selected as the best in these two categories. *Raphiolepis×delacourii* 'Georgia Charm' U.S. Plant Pat. No. 9,982 is a seedling which was produced from a cross between these two varieties. 'Georgia Charm' was used as the female or seed parent of the new cultivar *Raphiolepis×delacourii* 'Wilcor' which not only retained the leaf spot resistance and cold hardiness but also has a more compact growth habit and blooms two weeks later. This delayed bloom period can be advantageous in years when late frosts occur.

Classification:

Botanical: *Raphiolepis×delacourii* 'Wilcor'.

Parentage: Openly pollinated seedling of *Raphiolepis× delacourii* 'Georgia Charm'.

Commercial: Broadleaf evergreen.

Form: Dense and mounding.

Height: 2–3'.

Width: 3–4'.

Growth rate: Moderate slow under normal fertilization and moisture conditions. Semi-hardwood cuttings taken in late spring and through the summer produce rooted cuttings in three to four months in Griffin, Ga. Root development is vigorous and finely branched. In a period of six years from a rooted cutting, the plant reaches a height of 2 feet and a spread of 3 feet under normal growing conditions in Griffin, Ga. The plant normally grows at the rate of about 4 inches or more per year and reaches a height of 3 feet and a spread of 4 feet at maturity while maintaining a dense habit due to the abundant branch development.

Foliage: Alternate, simple, evergreen, elliptic to obovate, almost flat, and varying in size from 2⅛" to 2⅝" long and 1" to 1⅜" wide. The margins are entire to distally serrate. The petioles are ¼" to ⅞" long, 1/16" in diameter and Yellow-Green Group 146C. The midrib is prominent on both sides of the leaf and the smaller veins are prominent on the underside. Veins are depressed on the upper side giving a leathery appearance. These upper veins are Yellow-Green Group 146C. The base of the leaf is attenuate to cuneate and the apex is obtuse. The upper surface of the mature leaf is Yellow-Green Group 147A, glossy and glabrous. The underside is Yellow-Green Group 146C and matte. The underside veins are Yellow-Green Group 146A. These mature leaf colors are persistent throughout the winter. The immature leaves are tomentulose and pronounced with a reddish pigmentation, Greyed-Purple Group 183B, which changes to Yellow-Green Group 147A in three to four weeks in Griffin, Ga. The paired foliaceous stipules are 3/16" to ⅜" long and 1/16" to ⅛" wide. The upper surface is Yellow-Green Group 145A and the underside is Yellow-Green Group 145B. The stipules are caducous.

In 2002, the date of initial spring growth was March 18, in Griffin, Ga. After the initial spring flush there was almost continuous slow growth until fall, ending October 30, also in Griffin, Ga. When grown in full sun, the internode length of this plant is 5/16" to 9/16". When grown in light shade the internode length is 7/16" to ¾". As would be expected, a plant grown in the shade results in a taller, less dense plant with larger leaves.

Stems: The young shoots have a reddish pigmentation, Greyed-Purple Group 183B, and are tomentulose. The base of the immature petioles is also Greyed-Purple Group 183B. This new growth becomes Yellow-Green Group 146B in three to four weeks. After one or more years, the stems are generally grey (Greyed-Green Group 197B), glabrous, and rugose. The pith is solid and uniform.

Flowers: Perfect, single to semi-double, White Group 155D front and back, ⅞" in diameter by ½" in depth, fragrant, borne on dense, upright, tomentulose, 3 to 4" high and wide terminal panicles from late April to mid May. Each panicle has from 3–9 racemes which have from 1–6 flowers each, resulting in forty or more flowers per panicle. A mature plant can have 100 or more panicles. The flowers are attached to short pedicels which are ¼" to ½" in length and Yellow-Green Group 144A. The peduncle of each raceme is from ½" to 2½" long and Yellow-Green Group 144A. Each flower has 5–9 petals that are 7/16" long, 5/16" wide, obovate, and have obtuse tips. The flower has from 15 to 20 stamens, ¼" long, White Group 155C, with anthers Yellow Group 9B. The pollen matures to Yellow Group 9A. The pistil is 5/16" long, White Group 155C, and consists of two styles which are united and have ciliate margins. The base of the stamens and pistil change to a deep maroon color (Red-Purple Group 60B) two to three days after opening. Each flower has five sepals that are ⅛" long, 1/16" wide, lanceolate, and fused into a calyx. The calyx is ¼" in diameter, ⅜" in depth, Yellow-Green Group 144B, has ciliate margins and acuminate tips. In 2002, the blooming period began April 17, in Griffin, Ga. and ended May 12. The self-cleaning blooms last five to seven days on the plant in the garden.

Fruit: Drupaceous, globose, ¼" to ⅜" in diameter, 1 to 2 seeded. Summer fruit color Yellow-Green Group 144A ripen to Greyed-Purple Group 187A in the fall and persists as Black Group 202A attractively through the winter. Mature seeds are Greyed-Orange Group 163A beneath the pericarp.

Culture: Grows well in a wide range of conditions and tolerates sun to part shade. Grows in nearly any soil type, from moist to very dry and sand to clay. Responds well to mulching and medium applications of fertilizer; prefers ph 6 to 7. Very little pruning is needed. Adaptable to containers and above ground planters. Ideal for coastal regions and warmer parts of the Piedmont. Tolerates wind and salt spray. Propagated with semi-hardward cuttings in late spring through the summer.

Pests: None have been observed to date.

I claim:

1. A new and distinct variety of *Raphiolepis* plant named 'Wilcor', as illustrated and described.

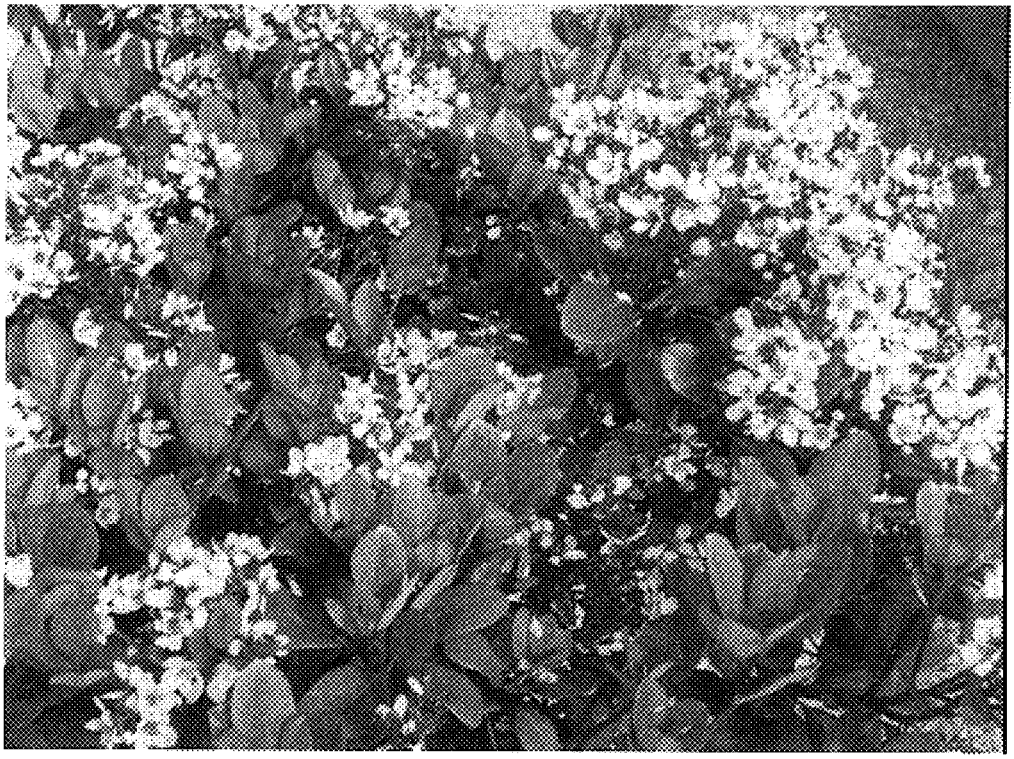
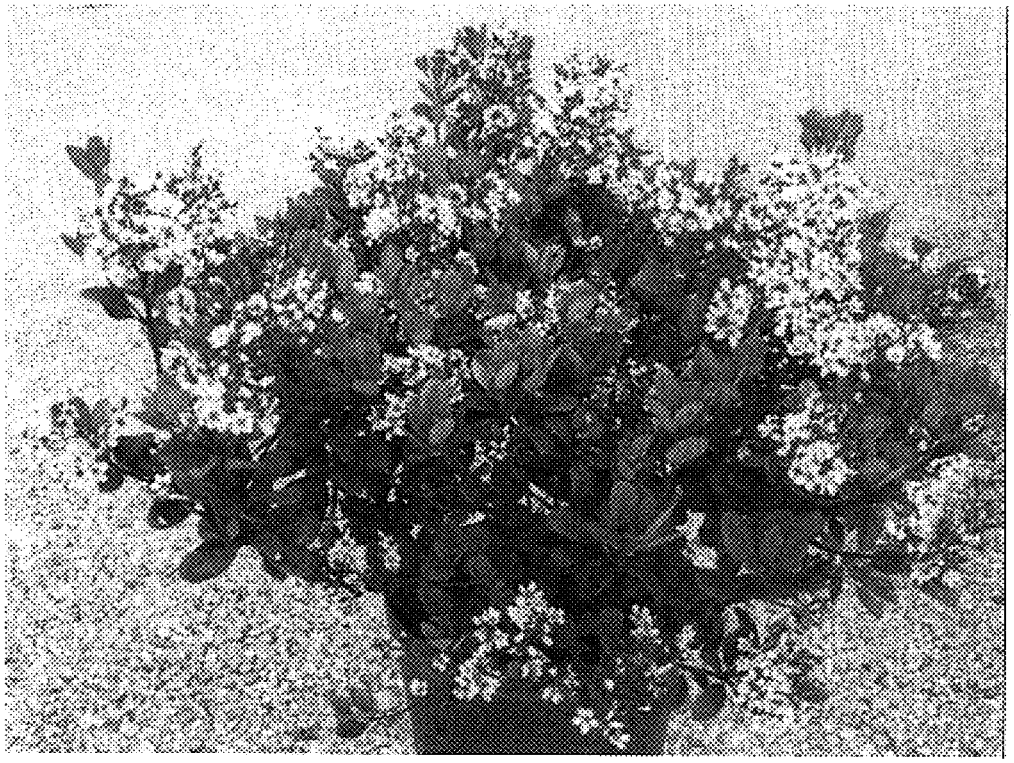

* * * * *